United States Patent [19]

Thelen et al.

[11] 4,115,462

[45] Sep. 19, 1978

[54] GAS PHASE AROMATIC HYDROGENATION USING PALLADIUM LITHIUM ALUMINUM SPINEL CATALYST

[75] Inventors: Hermann Thelen, Krefeld; Kurt Halcour; Wulf Schwerdtel, both of Leverkusen; Wolfgang Swodenk, Odenthal-Gloebusch, all of Germany

[73] Assignee: Bayer Aktiengesellschaft, Leverkusen, Germany

[21] Appl. No.: 788,868

[22] Filed: Apr. 19, 1977

Related U.S. Application Data

[62] Division of Ser. No. 586,838, Jun. 13, 1975, abandoned.

[30] Foreign Application Priority Data

Jun. 25, 1974 [DE] Fed. Rep. of Germany ....... 2430478

[51] Int. Cl.$^2$ .............................................. C07C 5/10
[52] U.S. Cl. .............................. 260/667; 260/677 H; 260/683.9
[58] Field of Search ...................... 260/667, 683.9, 677

[56] References Cited

U.S. PATENT DOCUMENTS

| | | | |
|---|---|---|---|
| 2,474,440 | 6/1949 | Smith et al. | 260/683.3 |
| 3,373,219 | 3/1968 | Krönig | 260/681.5 |
| 3,432,565 | 3/1969 | Kouwenhoven et al. | 260/667 |
| 3,459,657 | 8/1969 | Krönig et al. | 208/143 |
| 3,529,029 | 9/1970 | Pollitzer | 260/667 |
| 3,531,536 | 9/1970 | Gerhold | 260/667 |
| 3,649,703 | 3/1972 | Rausch | 260/667 |

*Primary Examiner*—Veronica O'Keefe
*Attorney, Agent, or Firm*—Burgess, Dinklage & Sprung

[57] ABSTRACT

Process for the preparation of cycloaliphatic hydrocarbons by gas phase hydrogenation of aromatic hydrocarbons in the presence of palladium catalyst, characterized in that palladium catalyst is used which contains the palladium applied to a support which comprises aluminium oxide of which at least 20% by weight, relative to the weight of the support, has been converted to lithium-aluminium spinel. The gas phase hydrogenation can be carried out at atmospheric pressure.

10 Claims, No Drawings

GAS PHASE AROMATIC HYDROGENATION USING PALLADIUM LITHIUM ALUMINUM SPINEL CATALYST

This is a division, of application Ser. No. 586,838, filed June 13, 1975 now abandoned.

BACKGROUND

The present invention relates to a process for the preparation of cycloaliphatic hydrocarbons by catalytic hydrogenation of aromatic hydrocarbons.

Processes have already been disclosed according to which aromatic hydrocarbons can be converted into the corresponding cycloaliphatic hydrocarbons by catalytic hydrogenation. For example, it is known that benzene can be hydrogenated to cyclohexane, toluene to methylcyclohexane, xylenes to dimethylcyclohexanes, ethylbenzene to ethylcyclohexane, isopropylbenzene to isopropylcyclohexane, naphthalene to tetrahydronaphthalene and/or decahydronaphthalene, and methylnaphthalene to methyltetrahydronaphthalene and/or methyldecahydronaphthalene. In some of these processes the hydrogenation is carried out in the liquid phase whilst in others hydrogenation is carried out in the gaseous phase. Combinations of gas phase and liquid phase hydroganations have also been described.

All previously disclosed processes for the hydrogenation of aromatic hydrocarbons, however, suffer from a series of disadvantages.

As regards the processes which are carried out in the gas phase, the following comments regarding the resulting disadvantages are made in German Patent No. 1,184,756, which relates to a process for the catalytic hydrogenation of aromatic hydrocarbons:

"The processes carried out in the gas phase give in practice only a low yield per unit volume of reaction zone, not only because of the low density of the treated product but also because of the difficulty of cooling this zone effectively. This leads either to the use of bulky apparatus which contain rather large and costly internal cooling pipelines, without however being able to avoid local heating of the catalyst, which reduces its activity, or leads to excessive dilution of the aromatic hydrocarbons, for example with the corresponding hydrogenation products. As a result, recycling installations for the hydrogenation products must be provided, which means that the equipment only provides a low yield." (German Patent No. 1,184,756, column 1, lines 26 to 42).

For example, U.S. Pat. No. 3,146,186 describes a gas phase hydrogenation for the conversion of benzene to cyclohexane in the presence of nickel catalysts, wherein the benzene, in a diluted form, is hydrogenated in two reactors arranged in series, with recycling of unconverted starting material. The performance of this process is rendered difficult by the great expense of the apparatus, the numerous separation and recycling processes, and its high operating pressures.

According to the process of U.S. Pat. No. 3,070,640, aromatic hydrocarbons are hydrogenated at pressures of 300 to 600 p.s.i. (about 21 to 42 bars) in the presence of platinum, nickel, palladium, rhodium, iron and/or Raney nickel, optionally on supports, as the catalyst, two catalyst systems, which differ in their metal content, being employed successively. The conduct of the reaction is also not uniform, since, in order to control the reaction temperature, the process is carried out initially with a diluted catalyst mass, that is to say with a less active catalyst, and subsequently with a more active catalyst (U.S. Pat. No. 3,070,640, column 2, lines 41 to 54). Accordingly, the performance of this process also entails considerable effort.

In carrying out the hydrogenation of aromatic hydrocarbons in the liquid phase, the catalyst is present in a suspended form and must therefore be introduced continuously into the reaction and again discharged continuously from the reaction vessel (DAS (German Published Specification) 1,116,218).

The disadvantages associated with the gas phase hydrogenation and liquid phase hydrogenation of aromatic hydrocarbons also arise in methods which are combinations of the gas phase method and liquid phase method (German Patent No. 1,184,756).

A process for the hydrogenation of aromatic hydrocarbons in the trickle phase is described in DOS (German Published Specification) 1,443,888, wherein the catalysts used are noble metals, especially platinum, rhodium and ruthenium, which are applied to alkaline earth metal carbonates and sulphates, silica, silicates and aluminum oxide as supports. Though only one reactor unit is necessary for the execution of this process, which results in a considerable advantage over the other processes for the catalytic hydrogenation of aromatic hydrocarbons, the process according to DOS (German Published Specification) 1,443,888 is not satisfactory since the catalysts lose their activity after a relatively short period of running and cannot be regenerated. Unsatisfactory working lives have also been recorded for the previously-known hydrogenations which are carried out in the liquid phase and in which catalysts of the Raney type, in a suspended form, are employed (for example DAS (German Published Specification) 1,116,218).

Finally, a further considerable disadvantage of all previously disclosed catalytic processes for the hydrogenation of aromatic hydrocarbons is that they are carried out at elevated pressure. In addition to the patent specifications mentioned, attention should, in this context, also be drawn to DAS (German Published Specification) 1,203,257 and U.S. Pat. No. 3,432,565.

THE INVENTION

According to the present invention, there is provided a process for the preparation of a cycloaliphatic hydrocarbon comprising effecting gas phase hydrogenation of an aromatic hydrocarbon in the presence of a catalyst comprising a metal of Group VIII of the periodic table (i.e. Co, Ni, Ru, Rh, Pd, Os, Ir or Pt), preferably palladium, carried on a support containing lithium-aluminium spinel. Preferably, the support is composed of aluminium oxide of which at least 20%, relative to the weight of the support, has been converted to lithium-aluminium spinel.

The hydrogenation is preferably carried out at a pressure equal to or slightly greater than atmospheric pressure.

The spinel used as support, according to the invention, may be obtained by reacting aluminium oxide with compounds of lithium. It is advantageous if the starting material for the preparation of the spinel is highly active aluminium oxide in particulate form and having a specific surface area of 200 to 350 m$^2$/g. However, it is also possible to use aluminium oxides of lower specific surface area as the starting material. It is possible to employ all the forms of aluminium oxide which are still absorbent and which, on calcining in the presence of lithium compounds, form lithium-aluminium spinels. The particulate aluminium oxide, for example in the shape of small cylindrical pieces, pellets or, preferably, spheres of dimensions from 1 to 10 mm, is impregnated or sprayed with the solution of lithium compound, and is then dried. Lithium hydroxide, lithium salts of inorganic acids, such as lithium nitrate and lithium chloride, and lithium salts of organic acids, such as lithium formate and lithium acetate, are examples of suitable lithium compounds.

During the impregnation or spraying with lithium salts, the salts can be converted into lithium hydroxide or lithium oxide by chemical transformation or by heating, prior to forming the spinel. The spinel formation is carried out at 900° to 1,300° C, and requires, for example, a period of 1 to 6 hours. Supports of high mechanical strength are thus obtained. If appropriate, stoichiometric formation of the spinel can be achieved by repeatedly carrying out the impregnation or spraying with the particular solution after an interpolated drying process and after possible calcinating.

The duration of the calcining process and the calcining temperature effect the specific surface area and the pore diameters of the finished supports. Catalyst supports with an average pore diameter of 200 to 800 A and specific surface areas, by the BET method, of 20 to 120 $m^2/g$ have proved suitable.

The palladium can be applied in a known manner to the support thus produced. For example, the palladium is applied to the support in amounts of 0.1 to 5% by weight, preferably 0.5 to 2% by weight, relative to the finished catalyst. For this purpose, the support is impregnated or sprayed, for example, with an aqueous palladium salt solution. All commercially available palladium compounds are suitable for the impregnation or spraying. Before the reduction of the palladium compounds to metallic palladium, the palladium compounds can be converted to palladium hydroxide or palladium oxide. The reduction of the palladium compounds to palladium, which follows can be carried out, for example, with formaldehyde or hydrazine in neutral or alkaline solution or with formic acid, hydrogen, carbon monoxide or ethylene. However, other methods of reduction can also be used. It is desirable that before using the catalysts thus prepared the anions of the palladium compound used which are present therein as a result of the process of preparation should be eluted with distilled water.

Any desired aromatic hydrocarbons are suitable as the starting material for the process according to the invention. For example, hydrocarbons of the benzene and naphthalene series which may be substituted by aliphatic side-chains can be employed. The aromatic nucleus can be substituted by one or more alkyl radicals with 1 to 4 carbon atoms. Examples of suitable hydrocarbons for the process according to the invention are benzene, oluene, ethylbenzene, n-propyl-benzene, cumene, xylenes, naphthalene, methylnaphthalene and ethylnaphthalene.

In general, the process according to the invention is carried out at temperatures of 200° to 350° C in the catalyst bed. It can be carried out at atmospheric pressure, e.g. atmospheric pressure plus the pressure necessary to overcome the resistance of the catalyst when passing the material to be hydrogenated through the reactor.

The aromatic hydrocarbon to be hydrogenated can be vaporised, and brought to the desired reaction temperature, before or in the reaction vessel. It can be of advantage not to vaporise completely the hydrocarbon intended for hydrogenation and to withdraw a small proportion as a bottom product.

In general, the gaseous starting mixture of aromatic hydrocarbon and hydrogen is preheated, for example to a temperature of 140° C, and passed from below into a tubular reactor containing the catalyst according to the invention. The catalyst can be subjected to 100–500 g, preferably 150–200 g, of aromatic hydrocarbon per litre of catalyst and per hour. The hydrogen is added in an excess, relative to the aromatic hydrocarbon. It may be added at any convenient point in the reaction systems. Preferably the hydrogen is added after the aromatic hydrocarbon has been preheated, for example after the vapouriser. The unconverted hydrogen can, after hydrogenation, be returned wholly or partially into the stream of input hydrogen.

The customary reactors can be employed as reaction vessels. For example, reaction tubes of 1 to 6 m length and 25 to 75 mm internal diameter are used, individually or as a tube bundle, and can be surrounded by a cooling jacket through which the heat of reaction can be removed. The reaction mixture which issues at the upper end of the reactor is cooled to the point that the hydrogenated product is condensed as completely as possible. In general, this requires temperatures of about 5°–10° C.

The cycloaliphatic hydrocarbon can be obtained in accordance with the process of the invention in a form sufficiently pure to enable it to be employed directly, without intermediate purification, in subsequent processes. For example, the cyclohexane obtained from benzene can be employed directly in the oxidation to give cyclohexanone/cyclohexanol.

If the unconverted hydrogen is returned, as circulating gas, to the input charge and the circulating gas contains inert gases, for example methane, it is desirable to withdraw a branch stream from the circulating gas. This can be necessary, for example, to give a hydrogen content, in the input gas, of at least 85% by volume.

Compared to the previously disclosed catalytic processes for the hydrogenation of aromatic hydrocarbons, the process according to the invention is distinguished by the following advantages:

1. Only a single reactor is required for carrying out the process.
2. The hydrogenation can be carried out at atmospheric pressure.
3. Repeated cycling of unconverted aromatic hydrocarbon is not necessary.
4. A single catalyst system, which enables long running times, complete conversions and high selectivities to be achieved, is employed. The following examples illustrate the invention.

EXAMPLE 1 — PREPARATION OF THE CATALYST 2.86 l of spherical-shaped Y-aluminum oxide of 4 to 6 mm diameter and having a specific surface area of about 250 $m^2/g$ and an average pore size diameter of about 300 A were impregnated at 30° with one litre of an aqueous solution into which 296 g of formic acid and 233 g of 54 % strength aqueous lithium hydroxide solution had been introduced successively, over a period of about one hour. The impregnated aluminium oxide was dried in vacuo at 150° C, again impregnated with the same solution, over a period of about 1 hour and again dried in vacuo at 150° C. The support material thus obtained was then calcined for 6 hours at 1.050° C, to give the spinel. The formation of the spinel was confirmed by an X-ray structure analysis. The finished support had a specific surface area of 25 m²/g and a mean pore width of 700 A. After impregnation over a period of about 1 hour with a solution of 82.7 g of palladium-II chloride, containing 110 g of hydrochloric acid (37% weight strength, and reduction with alkaline (10% by weight NaOH strength) formaldehyde (10% by weight CH₂O strength), elution of the chloride with distilled water and subsequent drying, the finished catalyst contained 1.8% by weight of palladium.

EXAMPLE 2 — GAS PHASE HYDROGENATION 2,000 ml of the 1.8% strength palladium catalyst according to Example 1 were introduced into a reaction tube of 50 mm internal diameter and 1 m length, which was provided with an oil-filled cooling jacket. After treating the catalyst with hydrogen at 150° to 200° C for a period of about 24 hours, the cooling jacket was cooled to 110°–120° C and thereafter 400 ml of benzene vapour together with 600 l of hydrogen were passed per hour over the catalyst. The heat of reaction is taken up by the cooling jacket of the reaction tube and conducted away. A marked reaction zone, which has a temperature maximum at about 240° to 250° C, became established. The hydrogen used-up for the hydrogenation reaction was continuously replaced by fresh hydrogen so that the amount of 600 l/hour of hydrogen were recycled as circulating gas. The conversion, relative to benzene, was 100%. The selectivity was approximately 100%, which thus corresponds to a yield of cyclohexane of about 100%.

The reaction product obtained contained 99.9% of cyclohexane.

EXAMPLE 3

When following the procedure in Example 2, 400 ml of toluene vapour and 600 l of hydrogen were passed hourly over the catalyst, a marked reaction zone again became established, which had a temperature maximum at about 230°–240° C. The molar ratio toluene:hydrogen was about 1:7; 600 l/hour of hydrogen were recycled as circulating gas. The conversion, relative to toluene, was 100%, with a selectivity of approximately 100%, which thus corresponded to yield of methylcyclohexane of about 100%.

The reaction product obtained contained 99.9% of methylcyclohexane.

What is claimed is:

1. In the process for the preparation of cycloaliphatic hydrocarbon by gas phase hydrogenation of the corresponding aromatic hydrocarbon by contacting the same with hydrogen and a catalyst consisting essentially of palladium, the improvement wherein said palladium is disposed on a support consisting essentially of aluminum oxide at least 20% by weight of which, based on weight of said support, is in the form of lithium aluminum spinel and the process is carried out at atmospheric pressure employing catalyst bed temperature of 200° to 350° C.

2. Process according to claim 1, wherein the catalyst contains 0.1 to 5% by weight of palladium, relative to the total weight of the catalyst.

3. Process according to claim 1, wherein the catalyst contains 0.5 to 2% by weight of palladium, relative to the total weight of the catalyst.

4. Process according to claim 1, wherein the support has an average pore diameter of 200 to 800 A.

5. Process according to claim 1, wherein the support has a specific surface area of 20 to 120 m²/g.

6. Process according to claim 1, wherein the aromatic hydrocarbon and hydrogen, are passed as an ascending gas stream through the catalyst bed.

7. Process according to the claim 1, wherein the catalyst contains 0.1 to 5% by weight of palladium, relative to the total weight of the catalyst, the support has a mean pore diameter of 200 to 800 A, the support has a specific surface area of 20 to 120 m²/g, the aromatic hydrocarbon and hydrogen, are passed as an ascending gas stream through the catalyst bed.

8. A process according to claim 1 wherein the process is carried out in a single reactor.

9. A process according to claim 8 wherein the process is carried out without any recycle of unconverted aromatic hydrocarbon.

10. A process according to claim 9 wherein the process is carried out employing a single catalyst system.

* * * * *

UNITED STATES PATENT OFFICE
CERTIFICATE OF CORRECTION

Patent No. 4,115,462            Dated September 19, 1978

Inventor(s) Hermann Thelen et al.

It is certified that error appears in the above-identified patent and that said Letters Patent are hereby corrected as shown below:

Column 1, line 27, "hydroganations" should read -- hydrogenations --.

Column 3, line 55, "oluene" should read -- toluene --.

Column 4, line 11 "systems" should read -- system --.

Column 4, line 56, "Y" should read -- $\gamma$ --.

Column 5, line 6, insert -- by -- before "weight".

*Signed and Sealed this*

*Sixth* Day of *February 1979*

[SEAL]

Attest:

RUTH C. MASON  
Attesting Officer

DONALD W. BANNER  
Commissioner of Patents and Trademarks